US00PP28673P2

(12) United States Plant Patent
Roberts

(10) Patent No.: US PP28,673 P2
(45) Date of Patent: Nov. 21, 2017

(54) MINT PLANT NAMED 'KLONDIKE'

(50) Latin Name: ***Mentha* sp.**
Varietal Denomination: Klondike

(71) Applicant: Essex Laboratories, Inc., Napavine, WA (US)

(72) Inventor: Donald D. Roberts, Independence, OR (US)

(73) Assignee: ESSEX LABORATORIES, LLC, Chehalis, WA (US)

( * ) Notice: Subject to any disclaimer, the term of this patent is extended or adjusted under 35 U.S.C. 154(b) by 0 days.

(21) Appl. No.: 14/999,749

(22) Filed: Jun. 21, 2016

(51) Int. Cl.
*A01H 5/04* (2006.01)

(52) U.S. Cl.
USPC ..... Plt./259

(58) Field of Classification Search
USPC ..... Plt./259
See application file for complete search history.

(56) References Cited

PUBLICATIONS

International Code of Nomenclature for Cultivated Plants, Scripta Horticulturae, No. 10, Eigth edition, 2009 (15 pgs total).*

Gobert, V., "Hybridization in the section *Mentha* (Lamiaceae) inferred from AFLP markers," Am. J. Bot., Dec. 2002, 89 (12), pp. 2017-2023.

Fuchs, Sabine, et al., "Biosynthesis of Menthofuran in *Mentha×piperita;* Stereoselective and Mechanistic Studies"; J. Agric. Food Chem., 1999, 47(10), pp. 4100-4105.

Dung, Jeremiah K.S., et al., "Evaluation of *Verticillium* Wilt Resistance in *Mentha arvensis* and *M. longifolia* Genotypes," Plant Disease, Oct. 2010, vol. 94, pp. 1255-1260.

Verma, R.S., et. al., "Essential Oil Composition of Menthol Mint (*Mentha arvensis*) and Peppermint (*Mentha piperita*) Cultivars at Different Stages of Plant Growth from Kumaon Region of Western Himalaya;" J. Medicinal and Aromatic Plants, India, 2010, vol. 1(1):pp. 13-18.

Zheljazkov, Yaltcho, et al., "Yield and Composition of Oil from Japanese Cornmint Fresh and Dry Material Harvested Successively," Agronomy Journal, 2010, vol. 102(6):pp. 1652-1656.

Roberts, D.D., and C. E. Homer, "Sources of Resistance to *Puccinia menthae* in Mint," Plant Disease, 1981, vol. 65, No. 4:pp. 322-324.

* cited by examiner

*Primary Examiner* — Susan McCormick Ewoldt
(74) *Attorney, Agent, or Firm* — Marger Johnson

(57) ABSTRACT

Mint selection 13-A36-13, denominated 'Klondike' peppermint is a new *Mentha* sp. cultivar that produces a unique essential oil, improved yield of essential oil, and increased resistance to mint rust and wilt.

3 Drawing Sheets

Latin name of the genus and species: *Mentha* sp.
Variety denomination: 'KLONDIKE'.

FEDERAL SPONSORSHIP

None

TYPE OF PLANT AND NAME OF VARIETY

The present invention relates to a new and distinct variety of peppermint plant developed from a parent of the species *M. arvensis*. The new variety will be identified as 'Klondike'.

BACKGROUND OF INVENTION

'Klondike' originated as a seedling from an open pollinated *M. arvensis*, breeding line 11-39-7, a female parent included with other *M. arvensis* and male fertile *M. piperita* plants in a polycross breeding program. Diploid *M. piperita* is sterile and only becomes fertile in the polyploidy state. The parent plants in the polycross breeding system were composed of selected fertile male and female genotypes based on certain desirable characteristics.

DISCOVERY AND ASEXUAL REPRODUCTION

This new mint was developed in a mint breeding program in which the primary objective was to develop a peppermint variety having a specific oil composition, increased yield, and resistant to mint diseases. The new variety is more resistant to mint wilt (soil-borne fungus *Verticillium dahliae*) and mint rust (air-borne fungus *Puccinia menthae*) than its parent. 'Klondike' has a higher yield of oil than the control variety, 'Black Mitcham', in test plots since 2013. This plant was selected from a population of mint seedlings in research plots on land near Monmouth, Oreg., and initially identified as 13-A36-13.

'Klondike' is asexually propagated, by tip cuttings and stolon sections, to maintain the cultivars genetic integrity and as a means of increasing the selection for commercial planting. Asexual propagation, by tip cuttings or stolon sections, is a common practice in commercial mint cultivation and serves as a means of propagating the normally sterile mint plant. 'Klondike' produces an abundant number of stolons to allow propagation by this means. The inventor has conducted asexual propagation of 'Klondike' for greenhouse and field planting at Monmouth, Oreg., since 2013 and the genotype comes true to form with each generation.

SUMMARY OF THE INVENTION

Mint selection 13-A36-13, denominated 'Klondike', is a new *Mentha* sp. cultivar that produces an essential oil similar in composition to that of commercially grown *M. arvensis* mint varieties. The essential oil is similar to standard mint oil in components composition but differs in the typical ratio of components. Organoleptically, it differs from typical *Mentha piperita* peppermint oil. It is more resistant to mint rust and mint wilt and yields more oil than current commercially grown *Mentha arvensis* varieties.

BRIEF DESCRIPTION OF THE FIGURES

The accompanying color figures show the typical, one-year-old, field grown vegetative growth of 'Klondike' and depicts the color as nearly as reasonably possible.

DESCRIPTION OF PLANT

Figure 1:
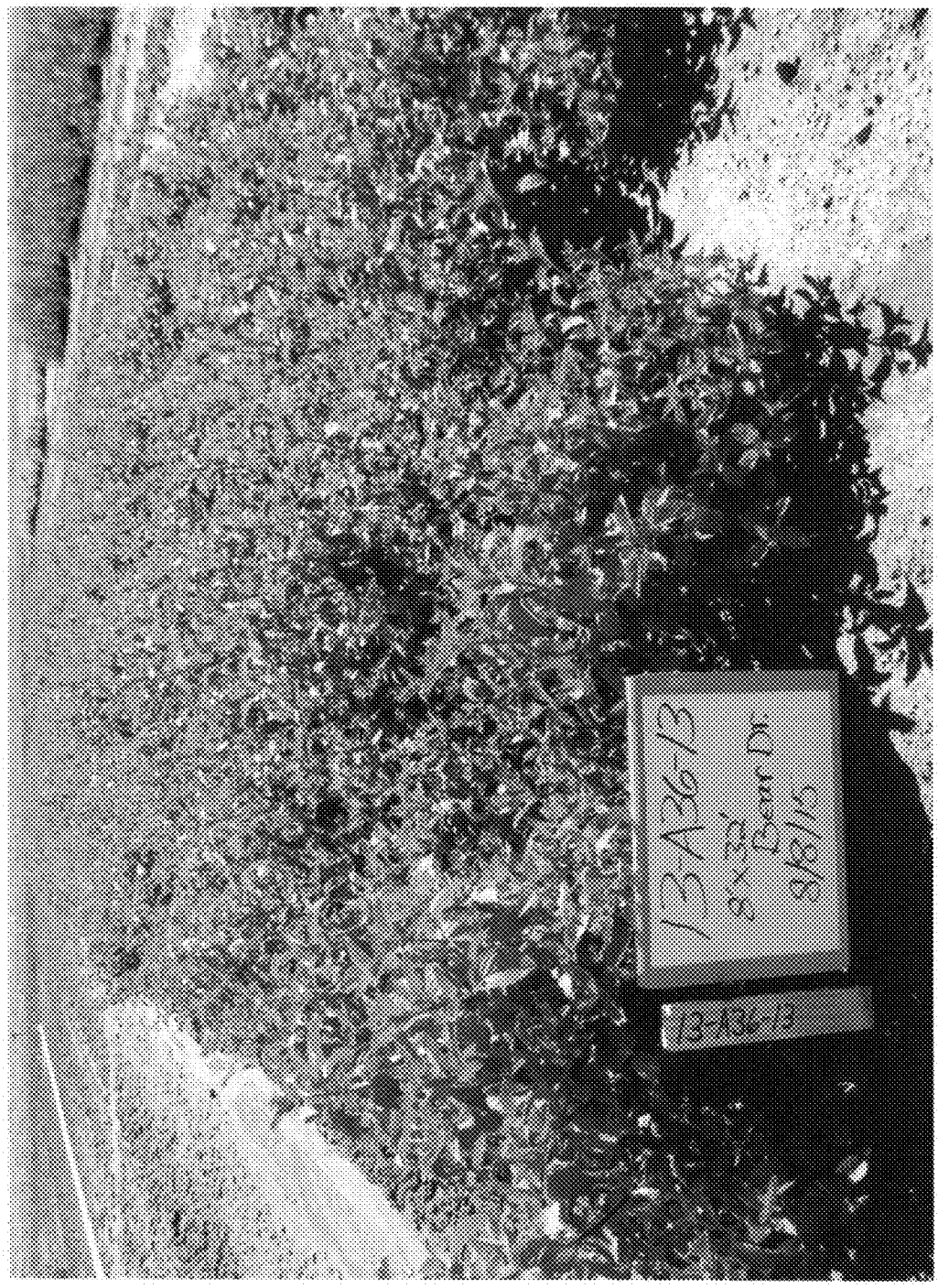
FIG. 1 illustrates a typical, one-year-old, field grown vegetative growth and color of 'Klondike'.
Figure 2:
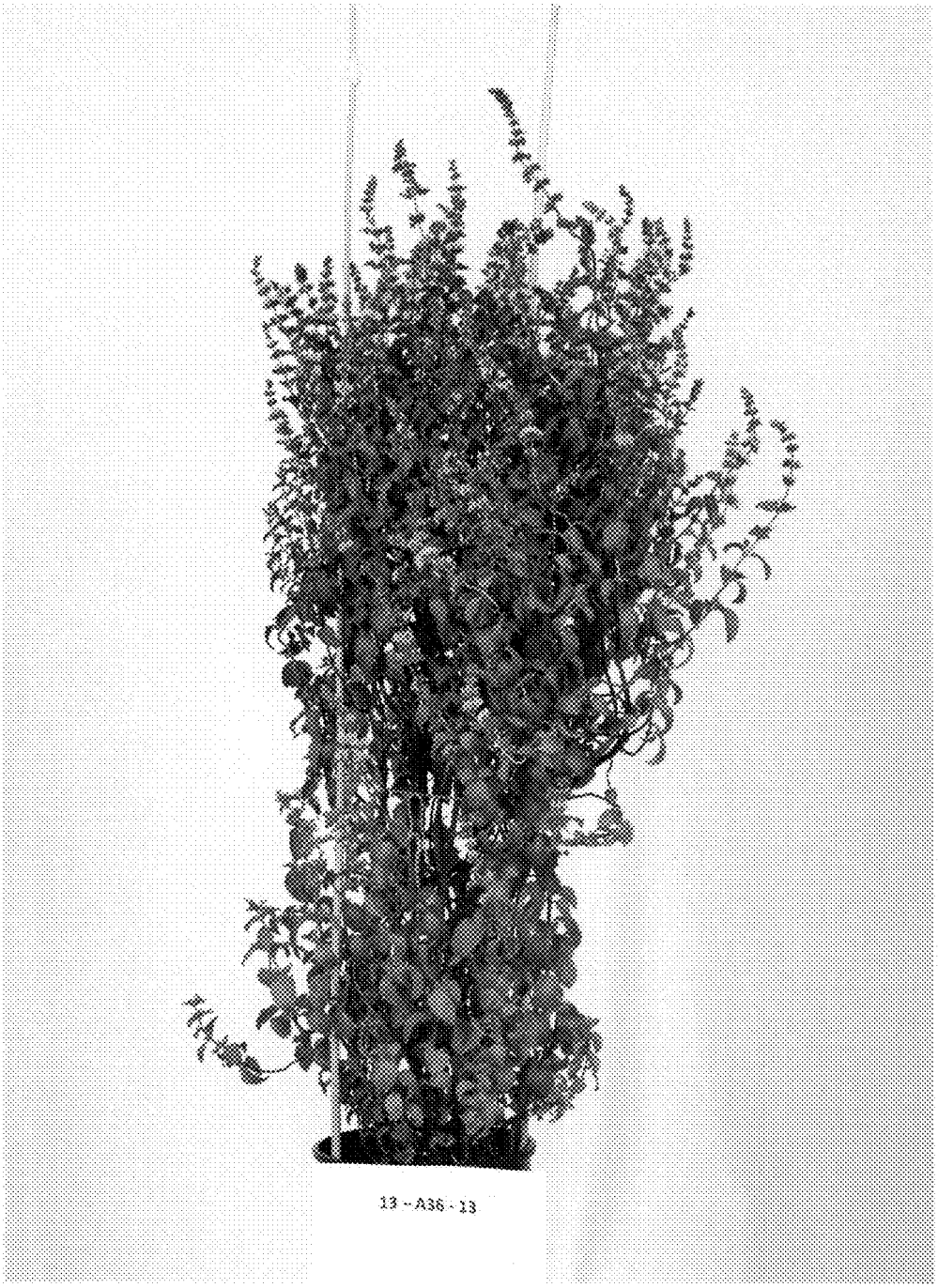
FIG. 2 illustrates the flowering pattern, multiple flowering shoots, inflorescence spike development, of my new mint plant in accordance with the present invention.
Figure 3:
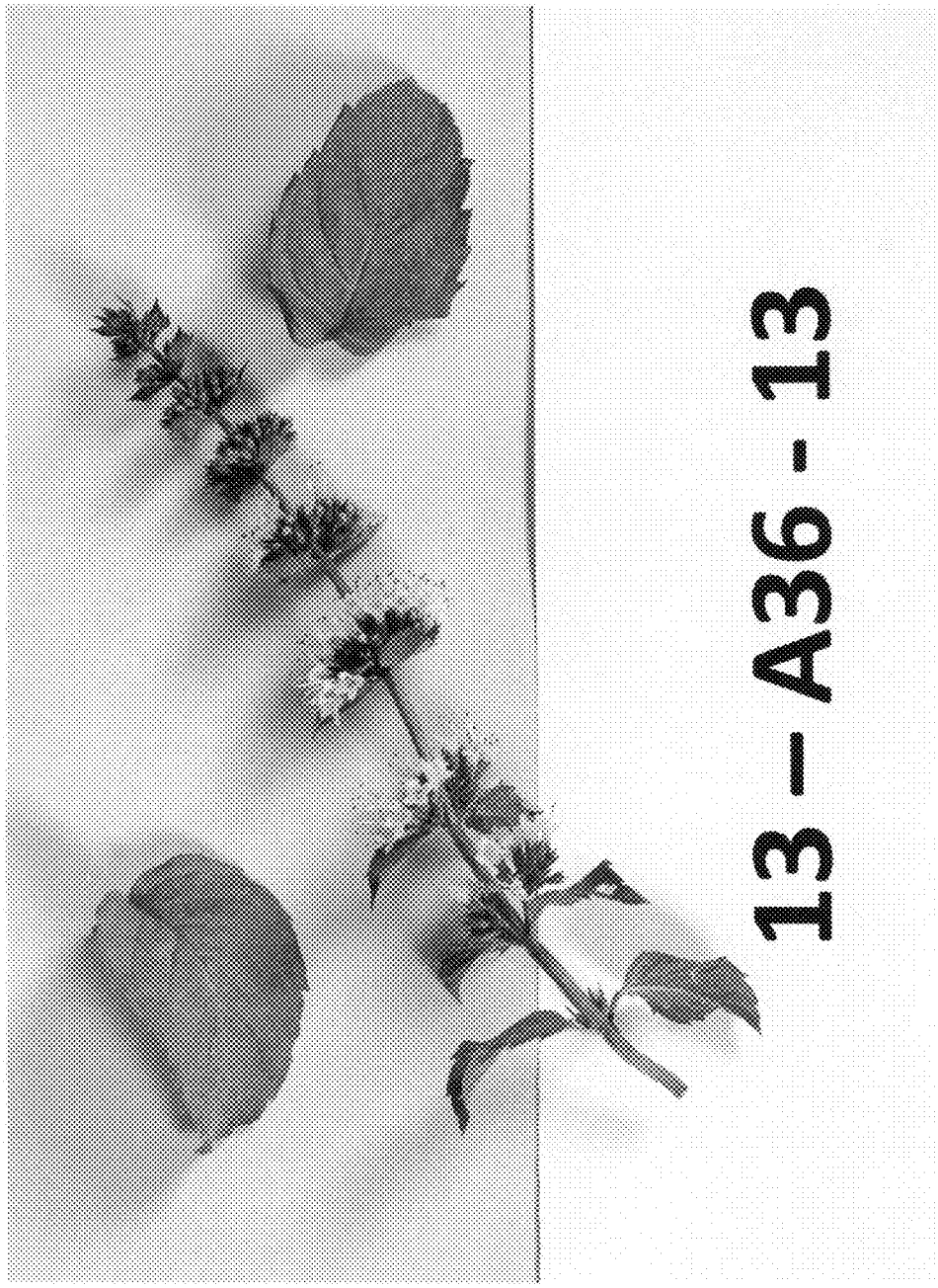
FIG. 3 illustrates the leaf shape and inflorescence of my new mint plant.

My new mint plant improves upon and is distinct from other mint plants in several characteristics, including but not limited to, the following:

1. The ability to produce an essential oil similar in composition to commercial cultivars of *M. arvensis* or *M. piperita* but with a different ratio of components;
2. A more compact plant but with a branching pattern similar to its parent;
3. A level of resistance to mint rust and wilt greater than that of its *M. arvensis* parent.

The essential oil extracted from 'Klondike' has a ratio of components that is different than that of commercial oil produced by 'Black Mitcham' peppermint (*M. piperita*) and *M. arvensis* as illustrated in Table 1. The concentration of menthone in oil of 'Klondike' is greater than that of commercial *M. arvensis*. There is a trace of menthofuran and pulegone present in the oil of 'Klondike' and absent in oil of its parent and commercial *M. arvensis*. Menthol concentration is higher in 'Klondike' than that of its parent and commercial *M. piperita*, but lower than commercial *M. arvensis*. Organoleptically, the oil of 'Klondike' is different than that of 'Black Mitcham' and *M. arvensis*, reflecting the difference in oil component ratios.

TABLE 1

A Comparison of 'Klondike' Oil collected from test plots near Monmouth, Oregon to that of its *M. arvensis* patent, Commercial *M. arvensis*, and Commercial *M. piperita* Oils. 1/

| Essential Oil Components | 11-39-7 *Mentha arvensis* Parent Seedling 2/ | 'Klondike' Seedling 2/ | Commercial *M. arvensis* | Commercial *M. piperita* |
|---|---|---|---|---|
| 1-Limonene | 2.8 | 2.6 | 3.0 | 1.7 |
| 1,8-Cineole | 1.3 | <1.0 | <1.0 | 4.9 |
| 1-Menthone | 14.0 | 15.0 | 7.3 | 19.4 |
| Menthofuran | 15.0 | 0.3 | 0.0 | 4.2 |
| Isomenthone | 2.3 | 2.5 | 3.6 | 3.1 |

TABLE 1-continued

A Comparison of 'Klondike' Oil collected from test plots near Monmouth, Oregon to that of its *M. arvensis* patent, Commercial *M. arvensis*, and Commercial *M. piperita* Oils. 1/

| Essential Oil Components | 11-39-7 *Mentha arvensis* Parent Seedling 2/ | 'Klondike' Seedling 2/ | Commercial *M. arvensis* | Commercial *M. piperita* |
|---|---|---|---|---|
| 1-Menthyl acetate | 5.2 | 7.8 | 2.9 | 5.3 |
| 1-Menthol | 47.0 | 60.0 | 73.3 | 44.6 |
| Pulegone | 0.0 | <1.0 | 0.0 | 2.1 |

The numbers listed in the above table are percentages based upon the analysis of the respective mint oils by gas chromatography. The percentages are determined by calculation of the relative peak areas.

1/ Commercial essential oils of *M. arvensis* and*M. piperita* were samples of what is typically produced by mint growers.

2/ The essential oil of *M. arvensis* parent seedling and 'Klondike' were collected from plants growing in test plots in 2012 and 2013, respectively.

TAXONOMIC DESCRIPTION OF 'KLONDIKE'

This new plant, under greenhouse and field growing conditions, is a bush type plant with lateral branches at each node of the main stems. The height of 'Klondike' is 145-150 cm and is equal to or greater than 'Black Mitcham' growing under similar conditions and will vary based on fertilizer, soil quality, and water application, amongst other known factors that affect growth patterns. Secondary and tertiary branching occurs to form a compact growth habit. The main stem at mid-plant (approximately between the eleventh and twelfth node) of a mature plant is 5.2-5.8 mm in width. The secondary branch stems are 1.4-1.6 mm in width. The average plant width is 30 cm and the average length of the main stem is 148 cm. The stems are square, glabrous, and a green color that matches The Fifth Edition Royal Horticultural Society Colour Chart 143B green group, with a moderate level of anthocyanin.

Mature leaves at the bottom of the plant are elliptic as are leaves on secondary branch stems. Leaves on upper mature plants, both main and secondary stems range from acute to lanceolate with an obtuse tip and oblique base (FIG. 1). Mid-main stem leaf size at flowering is 30-34 mm in width and 50-58 mm in length. Leaf size on secondary branches at flowering is 15-18 mm in width and 18-20 mm in length. Leaf petioles on the main stem leaves are on average 3.5-4.0 mm in length, 1.2-1.5 mm in diameter, and matching The Fifth Edition Royal Horticultural Society Colour Chart 143A to 143B. Leaves on the mid-main and lower stem tend to be less dentate than leaves on the upper plant. The main stem leaves have from 8 to 10 teeth on each side while the secondary branch leaves have 5-6 teeth on each side. The adaxial leaf surface is glabrous and light green in color, ranging from The Fifth Edition Royal Horticultural Society Colour Chart 144A to 146A in the yellow-green group classification. The abaxial leaf surface is sub-glabrous with oil glands distributed across the surface, and is light green in color ranging from The Fifth Edition Royal Horticultural Society Colour Chart 143A to 143B. The leaf has 5 lateral veins, more or less in parallel off the main vein that runs from the petiole to the tip of the leaf, and is the same color as the abaxial leaf surface. The veins are prominent in all leaves of 'Klondike'.

The inflorescence is a conspicuous spike with capitate flowers developing at the nodes of the spike stem. The average number of flowers per inflorescence of 'Klondike' did not vary significantly from the average number for mint plants in the closest varieties of *Mentha arvensis* and *Mentha piperita*, which have 2-40 flowers per inflorescence. The average length of the peduncle of 'Klondike' did not vary significantly from the average length for mint plants in the closest varieties of *Mentha arvensis* and *Mentha piperita*, in which peduncle length ranges from 0 mm (sessile) to 20 mm for mature blooms. Similarly, the color of the peduncle of 'Klondike' did not vary significantly from the peduncle colors for mint plants in the closest varieties of *Mentha arvensis* and *Mentha piperita*, which vary from the light green groups (138A-138C) to the greyed purple group (187A) as illustrated in The Fifth Edition Royal Horticultural Society Colour Chart. The cylindrical spikes are about 30-33 mm in diameter, indeterminate, and may be up to 50 mm in length. The capitate flowers are 15-20 mm in width and 10-15 mm in length. The flowers consist on average of five petals fused into a two lipped corolla. The adaxial and abaxial surface of the corolla are violet in color as illustrated in The Fifth Edition Royal Horticultural Society Colour Chart 85C in the violet group. The calyx is generally yellow-green and is 143A to 143B green group as illustrated in The Fifth Edition Royal Horticultural Society Colour Chart index. The gynoecium consists of a single pistil with two lobed stigma that is exserted. The androecium consists of four stamens, each with a distinct filament and anther. The dimensions of the reproductive organs of 'Klondike' did not vary significantly from the reproductive organ dimensions for mint plants in the closest varieties of *Mentha arvensis* and *Mentha piperita*, in which the style length ranges from 2.5-7 mm, the anther length is less than 1 mm, ranging from 0.4-0.5 mm, the filaments range from 0.5-4.0 mm in length, and the ovaries may be around 0.6 mm wide.

'Klondike' is female fertile and produces seed. Seed color is brown matching The Fifth Edition Royal Horticultural Society Colour Chart 200A to 200B brown group. The seed is oval in shape with a width of 0.4 mm to 0.5 mm, and a length of 0.6 mm to 0.8 mm.

While the plant that comprises the present invention has been described in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by increased resistance to mint rust and wilt and producing a unique essential oil.

* * * * *